United States Patent
Boland et al.

[11] Patent Number: 5,927,300
[45] Date of Patent: Jul. 27, 1999

[54] DENTAL CLEANSING IMPLEMENT

[75] Inventors: Bernhard Boland, Frankfurt; Werner Haczek, Idstein, both of Germany

[73] Assignee: Braun Aktiengesellschaft, Frankfurt, Germany

[21] Appl. No.: 09/006,330

[22] Filed: Jan. 13, 1998

Related U.S. Application Data

[63] Continuation of application No. 08/354,597, Dec. 13, 1994, Pat. No. 5,709,233.

[30] Foreign Application Priority Data

Dec. 23, 1993 [DE] Germany ............................. 43 44 110
Feb. 23, 1994 [DE] Germany ............................. 44 05 857

[51] Int. Cl.⁶ ................................................. A61C 15/00
[52] U.S. Cl. ......................... 132/322; 132/329; 433/118; 433/143
[58] Field of Search ..................... 132/321, 322, 132/329, 328; 433/143, 165, 166, 118, 125, 142

[56] References Cited

U.S. PATENT DOCUMENTS

| | | |
|---|---|---|
| 1,355,037 | 11/1920 | Dziuk . |
| 2,016,597 | 10/1935 | Drake . |
| 3,472,045 | 10/1969 | Nelsen et al. ............................. 433/142 |
| 3,559,292 | 2/1971 | Weissman ................................. 433/118 |
| 3,588,936 | 6/1971 | Duve . |
| 3,967,617 | 7/1976 | Krolik ...................................... 433/122 |
| 4,326,548 | 4/1982 | Wagner . |
| 4,347,839 | 9/1982 | Youngclaus ............................... 433/122 |
| 4,505,678 | 3/1985 | Andersson . |
| 4,576,190 | 3/1986 | Youssef . |
| 4,577,649 | 3/1986 | Shimenkov . |
| 4,617,718 | 10/1986 | Andersson . |
| 4,995,403 | 2/1991 | Beckman et al. ......................... 433/118 |
| 5,002,487 | 3/1991 | Tichy ....................................... 433/122 |
| 5,123,841 | 6/1992 | Millner . |
| 5,169,313 | 12/1992 | Kline . |
| 5,393,229 | 2/1995 | Ram . |
| 5,419,346 | 5/1995 | Tipp . |
| 5,573,020 | 11/1996 | Robinson . |

FOREIGN PATENT DOCUMENTS

| | | |
|---|---|---|
| A-0 354 352 | 2/1990 | European Pat. Off. . |
| 429447 | 9/1911 | France . |
| 243 224 | 2/1912 | Germany . |
| 17 66 651 C2 | 8/1971 | Germany . |
| 42 23 196 A1 | 1/1994 | Germany . |
| 42 26 659 A1 | 2/1994 | Germany . |

*Primary Examiner*—Todd E. Manahan
*Attorney, Agent, or Firm*—Fish & Richardson P.C.

[57] ABSTRACT

The invention is directed to a dental cleansing implement (101) having a thin, elongate shaft (102) comprising a free end portion (105) suitable in particular for insertion in the interproximal spaces and connected with a mounting portion (6) or the like. The mounting portion (6) is adapted to be coupled to an electric motor drive means of a handle member, and the cleansing implement is adapted to be rotated or oscillated about a shaft longitudinal center line (135). The free end portion (105) of the shaft (102) is made of a flexible material bent in the shape of a crescent (130), approximately.

30 Claims, 3 Drawing Sheets

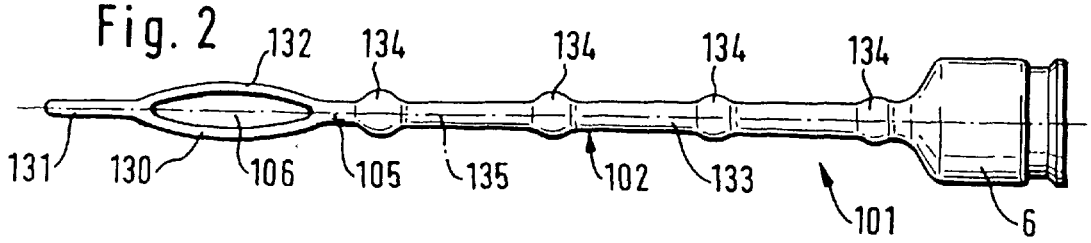
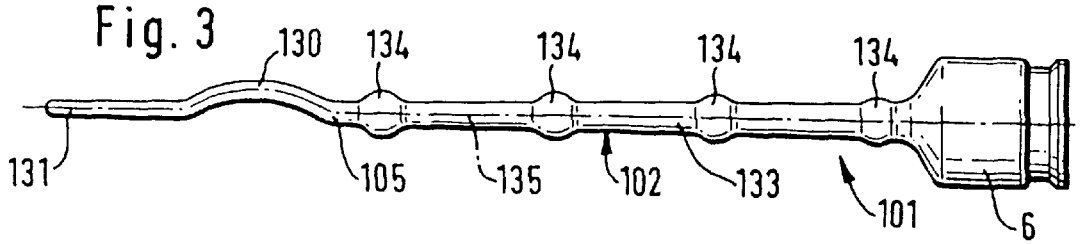
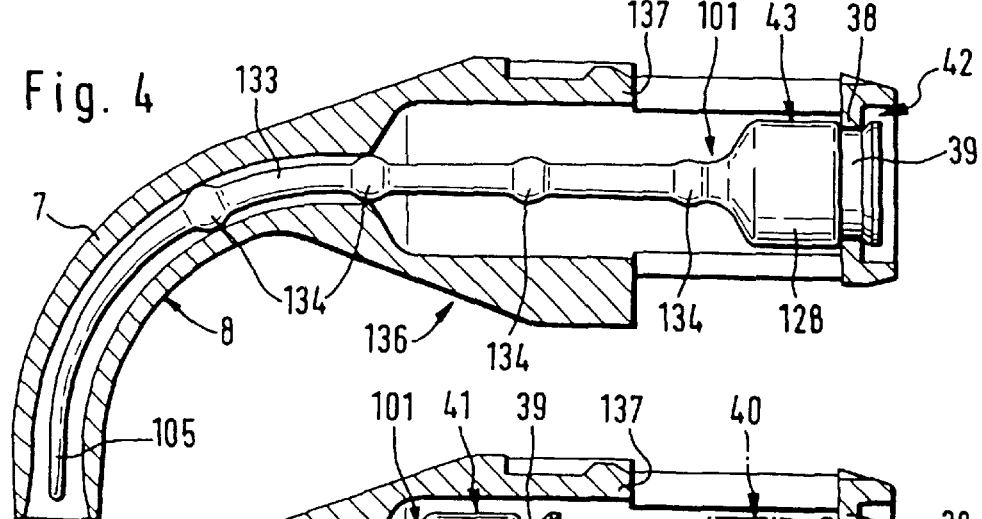
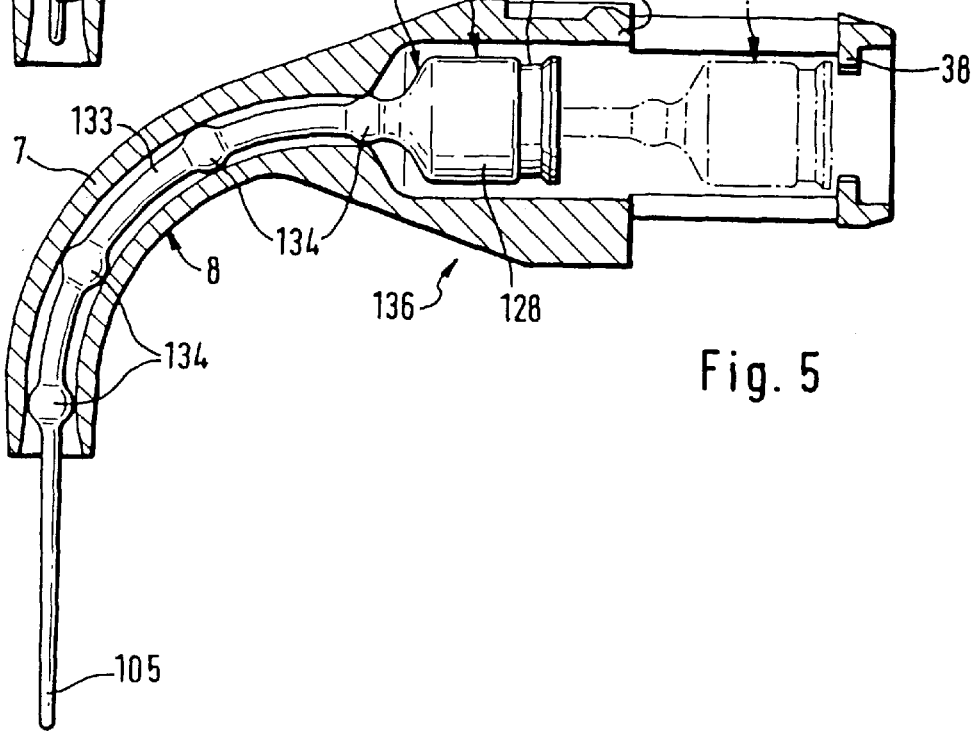

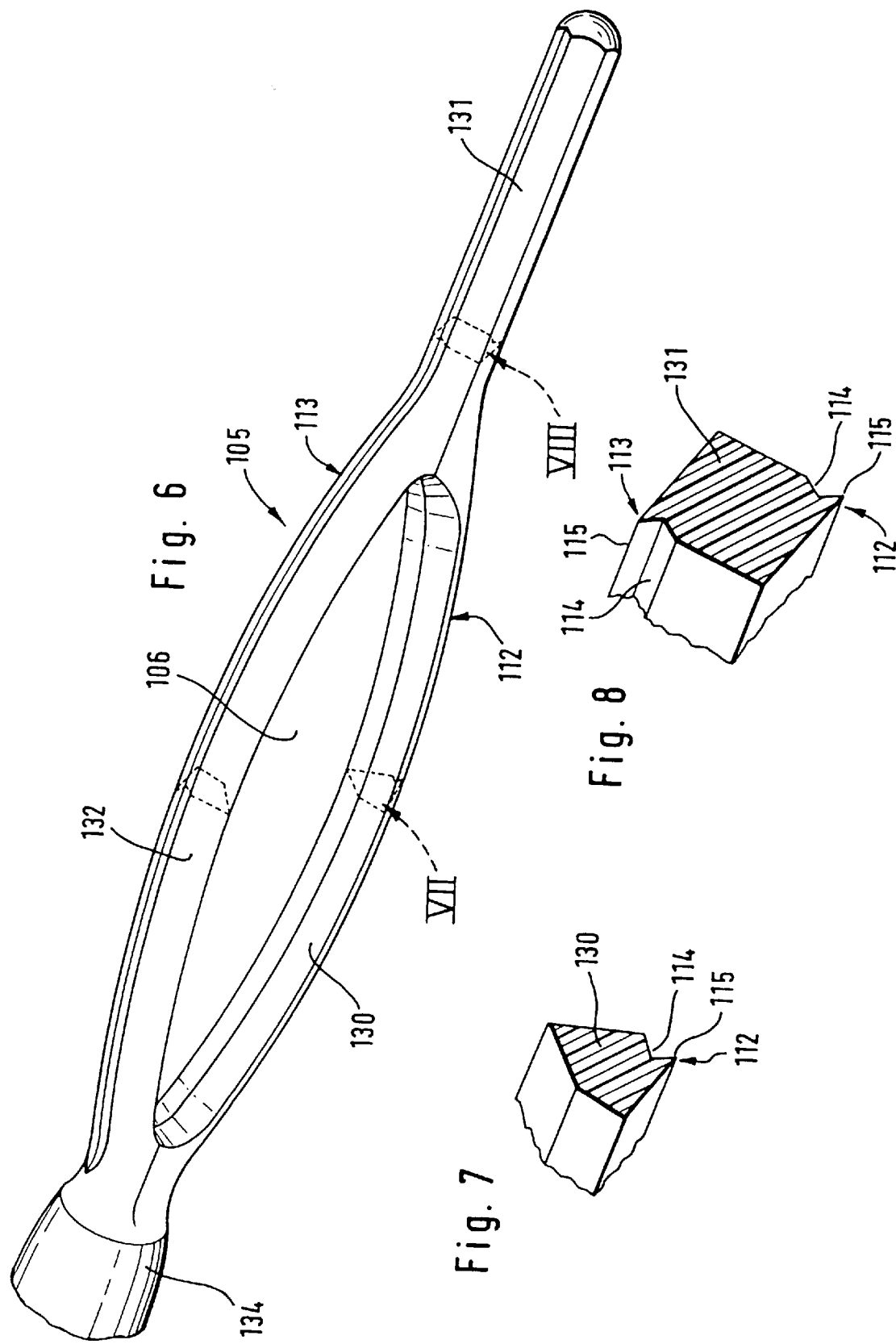

DENTAL CLEANSING IMPLEMENT

This application is a continuation of application Ser. No. 08/354,597, filed on Dec. 13, 1994, now U.S. Pat. No. 5,709,233.

This invention relates to a dental cleansing implement having a thin, elongate shaft comprising a free end portion suitable in particular for insertion in the interproximal spaces and connected with a mounting portion.

Such a dental cleansing device is known from prior European Patent No. EP 0 354 352 A1. The cleansing implement disclosed therein includes a thin stem provided with an abrasive coating for the removal of plaque. The stem is adapted to be located on a handle by means of a mounting structure. This prior known cleansing implement presents the problem that an effective cleaning action of the interproximal spaces can be accomplished only if the dimensions of the spaces correspond approximately to the diameter of the cleansing implement. Further, the manipulation of this hand-held and hand-operated cleansing implement is difficult and awkward with regard to its penetration between the user's teeth and also with regard to the need for the user's hand to set the cleansing implement in motion.

It is an object of the present invention to provide a cleansing implement by means of which an effective cleaning action of particularly the interproximal spaces as well as ease of manipulation are ensured.

According to the present invention, this object is essentially accomplished in that the mounting portion or the like is adapted to be coupled to an electric motor drive means of a handle member, that the cleansing implement is adapted to be rotated or oscillated about a shaft longitudinal center line, and that the free end portion of the shaft is made of a flexible material bent in the shape of a crescent, approximately.

The cleansing implement of the present invention affords the advantage of an effective dental cleaning operation and ease of manipulation. Because the cleansing implement is adapted to be coupled to an electric motor drive means and to be rotated or oscillated about a shaft longitudinal center line, it is ensured that the cleansing implement engages readily between the user's teeth, with the motor-induced motion of the cleansing implement ensuring an effective dental cleaning operation free from difficulty and fatigue. Because the free end portion of the shaft is made of a flexible material bent in the shape of a crescent, approximately, the cleansing implement conforms automatically to the individual dimensions of the interproximal spaces. When rotation or oscillation about the shaft longitudinal center line is imparted to the cleansing implement, the approximately crescent-shaped bent portion describes an outer circumferential surface of approximately barrel shape, with the diameter of this circumferential surface conforming automatically to the respective dimensions of the individual interproximal spaces owing to the flexibility of the shaft end portion. At all events, the cleansing implement of the present invention allows effective cleaning of interproximal spaces of various dimensions, because the free end portion makes contact with the tooth sides in the area of the approximately crescent-shaped bent portion also where interproximal spaces of different dimensions are involved.

Advantageously, at the head end a substantially straight leading portion adjoins the bent portion of the end portion, its shaft longitudinal center line being substantially identical with the axis of rotation. This facilitates the insertion of the cleansing implement into the interproximal spaces significantly.

Advantageously, the ratio of the length of the bent portion to the length of the end portion is about 1 to 2. With these dimensions a favorable compromise is accomplished between an optimum insertion of the cleansing implement and an effective dental cleansing operation.

In a further advantageous embodiment, the free end portion includes two adjacent bent portions providing an eyelet. By means of such a flexible cleansing eyelet the cleansing implement is in a position to conform automatically to different dimensions of interproximal spaces, with a balancing of masses being achieved by the converging arrangement of two adjacent bent portions so that, on the one hand, the cleansing implement is not appreciably deflected on account of unbalanced conditions, not even when exposed to high frequencies of rotation or oscillation. On the other hand, the use of two bent portions improves the cleaning action of the cleansing implement in individual cases. By virtue of the flexibility of the end portion, also the cleansing eyelet conforms automatically to the various dimensions of interproximal spaces. Both in this embodiment and in the embodiments referred to in the foregoing, it will be understood, of course, that also the tooth outer and inner surfaces can be cleaned, using, for example, a tangential motion of the cleansing implement relative to these surfaces.

Advantageously, the free end portion is made of a plastics material containing polyester, in particular, hytrel. Plastics materials of this type are characterized by a high fatigue strength under reversed bending stresses, whereby a high and constant resilience of the bent portion or eyelet is obtained. Further, bending of the complete cleansing shaft and a rotary or oscillatory drive of the cleansing shaft about the shaft longitudinal center line is also possible when these materials are selected.

Advantageously, an intermediate portion having one or several spherical enlargements is arranged between the end portion and the mounting portion. These spherical enlargements in the intermediate portion increase the torsional strength of the shaft of the cleansing implement, resulting in a prolonged life of the cleansing implement.

In an embodiment of the present invention, the free end portion includes at least one blade-shaped cleansing edge extending substantially parallel to the shaft longitudinal center line. This cleansing edge further aids in loosening in particular stubborn dental deposits as, for example, plaque.

An advantageous embodiment of the cleansing implement resides in that the free end portion has a length of about 5 mm, a thickness of about 0.3 mm, and a bent portion of about 0.5 mm or an eyelet with an inside width of about 1 mm.

In a particularly advantageous, independent embodiment of the present invention, the cleansing implement is encompassed by a receiving sleeve. This protects the cleansing implement from contamination and damage during periods of non-use, making it readily suitable for traveling use, for example.

Because the cleansing implement is slidably carried in the receiving sleeve and is movable from a storage position, in which the cleansing implement is substantially totally encompassed by the receiving sleeve, into an operating position in which the free end portion protrudes from the receiving sleeve, good manipulation of the cleansing implement is ensured. Being received in the sleeve, the cleansing implement is protected when not in use, and it can be simply pushed out of the receiving sleeve for use and also for engagement within the interproximal spaces.

Advantageously, the receiving sleeve includes a hollow cylindrical coupling portion having an adjoining guide sleeve in which the intermediate portion and, depending on the position of the cleansing implement, also the end portion of the cleansing implement are guided. By means of the guide sleeve, it is easy for the user to probe the interproximal spaces and, following its proper positioning, slide the cleansing implement out of the receiving sleeve for use, thus enabling it to enter the interproximal spaces with its free end portion to perform the desired cleaning function.

It is particularly advantageous that the inside diameter of the guide sleeve for the cleansing implement is only slightly greater than the diameter of the spherical enlargements of the intermediate portion. The spherical enlargements which are advantageously spaced uniformly apart along the length of the shaft act as bearings in the guide sleeve, thereby reducing sliding friction because only line contact exists between the spherical enlargements and the inner wall of the guide sleeve. As a result, torsional stresses in the shaft of the cleansing implement are materially reduced in use, thus prolonging the service life of the cleansing implement made of a plastics material of high fatigue strength under reversed bending stresses.

In an embodiment of the present invention, the guide sleeve includes a substantially circular-arc-shaped bent portion, with the circular arc covering an angular range of between 30 degrees and 150 degrees, preferably 90 degrees ±20 degrees. By this means, use of the dental cleansing device is facilitated, in particular for probing the interproximal spaces, for introducing the free end portion, and also for the subsequent cleaning action.

In a further embodiment of the present invention, the cleansing implement, together with the receiving sleeve, is suitable for use as a replacement part substituting a worn part. For replacement, the receiving sleeve together with the cleansing implement completely received therein is simply detached from the handle, and a new cleansing implement with receiving sleeve is substituted. Because the cleansing implement is completely received within the receiving sleeve, user contact with the potentially dirty cleansing implement is prevented from occurring during the replacement procedure.

In a particularly advantageous independent embodiment of the present invention, the cleansing implement is located in the receiving sleeve in a transit position by detent means, being movable from the transit position into the storage position or, where applicable, the operating position by coupling engagement with the drive means of the handle member. Because the cleansing implement is adapted to be releasably located within the receiving sleeve in a transit position in which the cleansing implement is totally encompassed by the receiving sleeve, damage to the cleansing implement prior to its first use is prevented. The replacement part thus allows the use of economical packaging means.

Advantageously, the cleansing implement is adapted to be coupled to an electric motor drive means of a handle member, with the drive shaft of the handle member being adapted to be connected with the cleansing implement in a non-rotating relationship and being slidably mounted in the longitudinal direction of the handle member. This thus enables the cleansing implement to be moved from the rest position into the operating position simply by displacing the drive shaft in the longitudinal direction of the handle member.

Because the drive shaft is coupled to a switch to energize and deenergize the electric motor drive means and is movable into an advanced position in the On-condition, a displacement of the switch results, on the one hand, in an energization of the electric motor drive means and, on the other hand, in a concomitant automatic movement of the cleansing implement from the position of rest into the operating position. This has the advantage of enabling the user to introduce the cleansing implement into the interproximal spaces with ease, this operation being supported still further by the rotary or oscillatory motion of the cleansing implement. For deenergization, the switch is returned to the Off-position, causing the electric motor drive means to be turned off while at the same time the cleansing implement is retracted within the receiving sleeve.

In an advantageous further development of the present invention, the drive shaft is acted upon by restoring means which, in the absence of switch actuation, automatically return the drive means to the Off-condition and/or cause the drive shaft to occupy the retracted position. It is thereby ensured that the dental cleansing device is automatically returned to the Off-condition when the user releases the switch. The spring then acts promptly to deactivate the electric motor drive means, urging at the same time the cleansing implement back into the receiving sleeve. This protects the user largely from the possibility of injury that may result from an improper handling of the cleansing device. It is also ensured that the cleansing implement is outside the receiving sleeve only during the cleansing operation proper, being at all other times positioned inside the receiving sleeve in a protected manner due to the action of the restoring means.

Further features, advantages and application possibilities of the present invention will become apparent from the subsequent description of embodiments illustrated in more detail in the accompanying drawings. It will be understood that any feature described and/or represented by illustration, whether taken alone or in any desired combination, constitutes the subject-matter of the present invention, irrespective of their summarization in the claims and their back-references.

In the drawings,

FIGS. 2 and 3 are views of two embodiments of the cleansing implement of the present invention;

FIGS. 4 and 5 are schematic views of a further embodiment of the cleansing implement of the present invention with the receiving sleeve, showing the cleansing implement in the transit and operating position, respectively;

FIG. 6 is a perspective view, on an enlarged scale, of the shaft of the cleansing implement according to the embodiment of FIG. 2; and FIGS. 7 and 8 are sectional views of the cleansing shaft of FIG. 6, taken on the planes VII and VIII, respectively.

Figure 1:
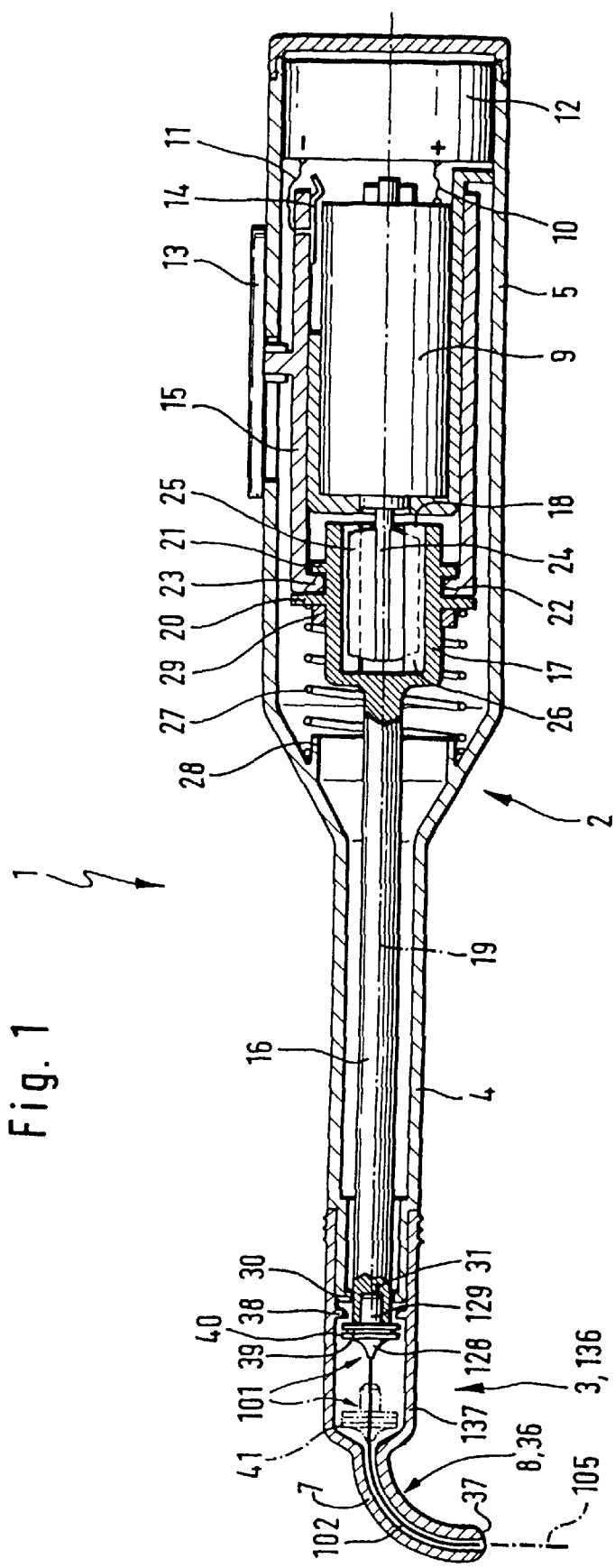
FIG. 1 is a schematic side view, partly in section, of an embodiment of a dental cleansing device incorporating the cleansing implement constructed in accordance with the present invention.

FIG. 1 shows a dental cleansing device 1 comprising a handle member 2 and an attachment 3. The handle member 2 is of an elongate configuration with a substantially circular cross-section. An intermediate portion 4 of the handle member 2 provided close to the attachment 3 is of a diameter smaller than that of a hand-held portion 5 provided remote from the attachment 3. The attachment 3 is equally of an essentially elongate configuration and has a substantially circular cross-section. The diameter of a coupling portion 137 of the attachment 3 at the end close to the handle member 2 corresponds to the diameter of the intermediate portion 4 of the handle member 2. At the end remote from the handle member 2, the attachment 3 is provided with a guide sleeve 7 of a reduced diameter which includes a bent portion 8. Accommodated in the hand-held portion 5 of the handle member 2, in particular fixedly located therein, is an electrically powered motor 9 connected to a source of power 12, for example, an accumulator, via electric conductors 10, 11. A longitudinally slidable switch 13 is arranged in the hand-held portion 5. Provided on the switch 13 is an electrically conductive contact means 14 which is connected to the power source 12 via the electric conductor 11. Further arranged on the switch 13 is a coupling member 15 serving to couple the switch 13 to a drive shaft 16.

The drive shaft 16 extends through the entire intermediate portion 4 into the hand-held portion 5 and has at its free end close to the motor 9 in the area of the handle member 2 a cup-shaped receptacle 17 with an opening 18. The motor 9, the drive shaft 16 and the cup-shaped receptacle 17 are concentrically arranged with a common axis 19, with the opening 18 of the cup-shaped receptacle 17 being provided at the end close to the motor 9. Projecting radially outwardly from the outside of the cup-shaped receptacle 17 are two relatively spaced annular collars 20, 21 defining an annular groove 22 therebetween for engagement by an annular collar 23 of the coupling member 15 projecting inwardly therefrom. As a result, a displacement of the switch 13 in the longitudinal direction, in addition to having the effect of turning the device on and off, also produces a displacement of the cup-shaped receptacle 17 together with the drive shaft 16 in the longitudinal direction of the axis 19. While the annular collar 23 is fixed in place in the circumferential direction, the cup-shaped receptacle 17 with its annular groove 22 is rotatable relative to the annular collar 23. The cup-shaped receptacle 17 is thus capable of rotating about the axis 19 irrespective of the position of the switch 13. It will be understood that the added provision of a bearing or the like, not shown, may be envisaged in the area of the annular collar 23 and the associated annular groove 22 to reduce friction.

At the end of the cup-shaped receptacle 17 close to the opening 18, a motor shaft 24 extends from the motor 9, which shaft is arranged concentrically with the axis 19 as is the motor 9. The motor shaft 24 is provided with at least one, preferably however, several vanes 25 projecting radially outwardly. The cup-shaped receptacle 17 has in its interior a corresponding number of longitudinal ribs 26 projecting radially inwardly. The vanes 25 extend through the opening 18 into the interior of the cup-shaped receptacle 17, engaging in the space between the longitudinal ribs 26. In this arrangement, the vanes 25 and the longitudinal ribs 26 overlap along an axial length which is greater than the maximum possible length of displacement of the switch 13 in the longitudinal direction.

Therefore, a rotary or oscillatory motion of the motor shaft 24 is transmitted through the vanes 25 and the longitudinal ribs 26 to the cup-shaped receptacle 17 and to the drive shaft 16. Owing to the overlapping arrangement of the vanes 25 and the longitudinal ribs 26 in the longitudinal direction, the cup-shaped receptacle 17 is displaceable by means of the switch 13, without the driving relationship between the motor shaft 24 and the drive shaft 16 being interrupted. It will be understood that this coupling structure may also be configured in a different manner, using, for example, a suitable gearing or the like. Seated between the side of the annular collar 20 facing the intermediate portion 4 of the handle member 2 and the transition area between the hand-held portion 5 and the intermediate portion 4 is a spring 27 which is located in position by means of support walls 28, 29. The spring 27 produces a force acting in opposition to a displacement of the switch 13 towards the attachment 3. As a result, the spring invariably urges the switch 13 and thus the drive shaft 16 automatically into a direction away from the attachment 3, into a storage position 40, without any force acting from outside.

At the end of the handle member 2 close to the attachment, the drive shaft 16 is guided by an annular collar 30 projecting inwardly from the handle member 2. The drive shaft 16 projects from the intermediate portion 4 by a small amount, its free end being provided with a bore 31 extending substantially concentrically with the axis 19.

In the attachment 3 fitted to the handle member 2, a cleansing implement 101 is longitudinally slidably received. The cleansing implement 101 includes a cleansing shaft 102 of an elongate and thin configuration. Preferably, the cleansing shaft 102 is about 30 mm long and has a diameter in the range from 0.3 mm to 0.5 mm, approximately. The cleansing shaft 102 is made of a plastics material, in particular a polyester elastomer as, for example, hytrel. The cleansing shaft 102 is flexible, enabling it to be bent by an angle of up to 150 degrees and more, also as it rotates about its longitudinal axis.

At its end close to the drive shaft 16, the cleansing implement 101 includes a circular base 128 connected to the cleansing shaft 102. A pin 129 is connected to the base 128. The pin 129 is received in the bore 31 of the drive shaft 16. The pin 129 and the bore 31 may be press-fitted together or, alternatively, their cross-sectional shapes may be conformed to each other, for example, in the form of a polygon or the like. The pin 129 is inserted in the bore 31 in a non-rotating relationship thereto, with the cleansing shaft 102 extending from the base 128 to the guide sleeve 7 and being passed therethrough.

Because of the bent portion 8 of the guide sleeve 7, the cleansing shaft 102 received in the guide sleeve 7 is equally provided with a correspondingly bent portion 36. This portion may be bent at angles of up to 150 degrees and more, preferably an angle of 90 degrees +20 degrees is provided. The free end of the guide sleeve 7 includes an essentially hemispherical rounded portion 37 having a diameter in the range from 1 mm to 4 mm, approximately, in particular 2.5 mm. The dental cleansing device 1 shown is adapted to be set to an Off-condition in which the cleansing implement 101 is in a storage position 40, and to an On-condition in which the cleansing implement 101 is in an operating position 41. FIG. 1 shows both positions 40, 41 jointly in solid and, respectively, broken lines. The drive shaft 16 and the other parts of the dental cleansing device are, however, all shown in the storage position 40.

FIGS. 4 and 5 show, on an enlarged scale, the cleansing implement 101 and the associated receiving sleeve 136 in a further embodiment of the present invention. In FIG. 5, the broken lines illustrate the cleansing implement 101 in its storage position 40, while the lines drawn in full illustrate the operating position 41 thereof. In the storage position 40, the cleansing implement 101 and in particular the cleansing shaft 102 are fully received in the interior of the receiving sleeve 136 or the attachment 3. The base 128 and the pin 129 are in the immediate proximity of the end of the handle member 2 close to the attachment 3. In contrast thereto, when in the operating position 41, the cleansing implement 101 is not fully received inside the receiving sleeve 136. The end portion 105 of the cleansing shaft 102 projects from the free end of the guide sleeve 7. Preferably, the end portion 105 has a length of 10 mm to 15 mm, approximately, in particular 12 mm.

When the switch 13 is in its Off-position, the contact means 14 does not make contact with the mating contact means of the motor 9. Under these conditions, the motor shaft 24 and thus the drive shaft 16 and the cleansing implement 101 do not rotate or oscillate. By virtue of the force exerted by the spring 27, also the drive shaft 16 is in the retracted position illustrated in FIG. 1. This also causes the cleansing implement 101 to be in its storage position 40 in which it is totally encompassed by the attachment 3. When a user then shifts the switch 13 in the longitudinal direction towards the attachment 3, the contact means 14 will energize the motor 9, and the motor shaft 24 will be caused to rotate or oscillate about the axis 19. By means of the vanes 25 and the longitudinal ribs 26, this rotary motion will be transmitted to the drive shaft 16 as well as to the cleansing implement 101 coupled thereto. Rotation or oscillation about its longitudinal center line is thereby imparted to the cleansing shaft 102 provided with the bent portion 36. Simultaneously with the displacement of the switch 13 to the On-position, the drive shaft 16 will be displaced outwardly in the direction of the axis 19 through the annular collar 23 and the annular groove 22. This motion will be transmitted to the cleansing implement 101 coupled to the drive shaft 16, causing it to be moved into the operating position 41 when the cleansing device 1 is turned on. The cleansing implement then extends with its end portion 105 out of the guide sleeve 7, ready for cleaning the tooth surfaces. Advantageously, with the dental cleansing device still in the Off-position, the guide sleeve 7 is first positioned against the interproximal spaces to be cleaned before moving the switch 13 to the On-position. This facilitates the insertion action of the end portion 105 of the cleansing implement 101 significantly. When the user releases the switch 13, the spring 27 will return the switch 13 to the Off-position. This also causes the cleansing implement 101 to return to its storage position 40 automatically. The contact means 14 is disengaged from the motor 9, so that the motor is off.

FIG. 4 shows the attachment 3 or the receiving sleeve 136 together with the cleansing implement 101 in a transit position 43. For this purpose, the receiving sleeve 136 has about centrally in the coupling portion 137 an inwardly projecting annular collar 38. The base 128 of the cleansing implement 101 is provided with an annular groove 39 adapted to register with the annular collar 38. In the transit position 43 shown, the annular collar 38 is in locking engagement with the annular groove 39, causing the cleansing implement 101 to be detachably located within the receiving sleeve 136. In this transit position 43, the attachment 3 or the receiving sleeve 136 are commercially available as a replacement part, being encased, for example, in a blister packing, and can be purchased by the customer to replace worn cleansing implements 101. The cleansing implement 101 is thus received in the attachment 3 in a safe and protected manner. When the attachment 3, with the cleansing implement 101 in locking engagement therewith, is fitted to the handle member 2, the pin 129 will be inserted into the bore 31. Shortly before the attachment 3 is completely push-fitted to the handle member 2, the annular collar 38 will urged out of its engagement with the annular groove 39, so that the cleansing implement 101, rather than being held captive inside the attachment 3, is then arranged therein in a slidable relationship.

FIG. 2 shows a first embodiment of a cleansing implement 101 in which the cleansing shaft 102 is held on a mounting portion 6. Adjoining the mounting portion 6, the cleansing shaft 102 includes an intermediate portion 133 having several, in particular equidistantly spaced, enlargements 134. The intermediate portion 133 has an adjacent end portion 105. This end portion 105 possesses two adjacent bent portions 130, 132 defining an eyelet 106. The bent portions 130, 132 continue in a leading portion 131. With the exception of the bent portions 130, 132, the cleansing implement 101 is configured so as to be substantially symmetrical about a shaft longitudinal center line 135. The cleansing implement 101 is made of a flexible plastics material, for example, hytrel, which is capable of withstanding high bending stresses with repeated stress reversals without showing any signs of fatigue.

In contrast thereto, FIG. 3 shows a cleansing implement 101 having solely one single bent portion 130 practically defining "half" an eyelet 106. An oscillating or rotating motion of the cleansing implement 101 about its shaft longitudinal center line 135 dynamically complements, so to speak, the eyelet of the embodiment of FIG. 2. The cleansing implement 101 of the embodiment of FIG. 3 has the advantage of affording greater ease of manufacture. This will become apparent particularly when considering that the thickness of the cleansing implement 101 is of the order of about 0.3 mm in the area of the free end portion, with the bent portion 130, 132 having a value of about 0.5 mm +0.2 mm.

In FIG. 6, the end portion 105 of a cleansing implement 101 of FIG. 2 is illustrated on an enlarged scale. Two cleansing edges 112, 113 extend along the full length of the eyelet 106 and in particular along the leading portion 131. According to FIGS. 7 and 8, the cleansing edges 112, 113 are formed by notches 114, so that blade-shaped ridges 115 are obtained. The notches 114 are arranged such that the ridges 115 point to the same direction of rotation. While the bent portions 130, 132 are of a substantially triangular profile, the leading portion 131 has an approximately square profile.

As becomes apparent particularly from FIG. 5, the spherical enlargements 134 on the intermediate portion 133 of the cleansing implement 101 serve a bearing function to reduce the sliding friction in the guide sleeve 7, because only line contact occurs between the cleansing implement 101 and the guide sleeve 7.

Still further, it is advantageous to superimpose a reciprocating motion acting in the direction of the shaft longitudinal center line 135 upon the rotary or oscillatory motion of the cleansing implement 101, whereby the cleaning effect is further augmented and, where applicable, the insertion of the cleansing implement 101 into the interproximal spaces is facilitated.

We claim:

1. A dental cleansing instrument, comprising:
   a handle member including a housing and an electric motor drive; and
   a cleansing implement including an elongate member having a mounting portion structured for removably coupling with the electric motor drive, and
   a thin, elongate shaft characterized by a longitudinal center line and having a free end portion structured for insertion in interproximal spaces,
   wherein the mounting portion is coupled to the electric motor drive which during operation
   (1) causes the free end portion to at least one of rotate or oscillate and having an axis of rotation or oscillation which coincides with the shaft longitudinal center line, and
   (2) also causes the free end portion to perform a superimposed reciprocating motion in the direction of the shaft longitudinal center line.

2. The implement of claim 1 wherein the free end portion of the shaft comprises a flexible, resilient material.

3. The implement of claim 1 wherein the free end portion is made of a plastic material containing polyester.

4. The implement of claim 3 wherein the plastic material contains hytre.

5. The implement of claim 1 wherein the free end portion includes a blade-shape cleansing edge extending substantially parallel to the shaft longitudinal center line.

6. The implement of claim 1 further including a receiving sleeve encompassing the elongate shaft.

7. The implement of claim 6 wherein the elongate member is slidably carried in the receiving sleeve and is movable from a storage position, in which the elongate shaft is substantially totally encompassed by the receiving sleeve, into an operating position in which the free end portion protrudes from the receiving sleeve.

8. The implement of claim 6 wherein the receiving sleeve includes a hollow cylindrical coupling portion having structure for coupling to a housing portion of the handle member, and an adjoining guide sleeve in which an intermediate portion of the elongate shaft is guided.

9. The implement of claim 8 wherein the guide sleeve includes a substantially arc-shaped bent portion.

10. The implement of claim 9 herein the arc-shaped bent portion covers an angular range of between 30 degrees and 150 degrees.

11. The implement of claim 9 wherein the arc-shaped bent portion covers an angular range of 90 degrees ±20 degrees.

12. The implement of claim 6 wherein the elongate shaft together with the receiving sleeve are structured to be removably mounted to the handle member as a unit.

13. The implement of claim 1 wherein the electric motor drive includes a drive shaft slidably mounted in a longitudinal direction of the handle member, with the drive shaft being adapted to be connected with the mounting portion in a non-rotating relationship.

14. The implement of claim 13 further including a switch coupled to the drive shaft, said switch energizing and deenergizing the electric motor drive to an on-condition and an off-condition, respectively.

15. The implement of claim 14 further including a restoring element which acts upon the drive shaft to automatically return the motor drive to the off-condition.

16. The implement of clam 15 further including a restoring element which acts upon the drive shaft to automatically cause the drive shaft to occupy a retracted position.

17. A dental cleansing implement for coupling to a handle member with an electric motor drive, the cleansing implement comprising:

an elongate member including
a thin, elongate shaft having a free end portion structured for insertion in interproximal spaces,
a mounting portion connected with the shaft, the mounting portion including structure adapted to be coupled to the electric motor drive, and
an intermediate portion of the shaft between the free end portion and the mounting portion, the intermediate portion including a spherical enlargement having a bearing surface which reduces sliding friction when the intermediate portion is within a guide sleeve.

18. The implement of claim 17 wherein the free end portion of the shaft comprises a flexible, resilient material.

19. The implement of claim 17 wherein the free end portion is made of a plastic material containing polyester.

20. The implement of claim 19 wherein the plastic material contains hytre.

21. The implement of claim 17 wherein the free end portion includes a blade-shape cleansing edge extending substantially parallel to a shaft longitudinal center line.

22. The implement of claim 17 further including a receiving sleeve encompassing the elongate member.

23. The implement of claim 22 herein the elongate member is slidably carried in the receiving sleeve and is movable from a storage position, in which the elongate member is substantially totally encompassed by the receiving sleeve, into an operating position in which the free end portion protrudes from the receiving sleeve.

24. The implement of claim 22 wherein the receiving sleeve includes a hollow cylindrical coupling portion having structure for coupling to a housing portion of the handle member, and an adjoining guide sleeve in which the intermediate portion is guided.

25. The implement of claim 24 wherein the spherical enlargement has a diameter slightly less than an inside diameter of the guide sleeve.

26. The implement of claim 24 wherein the guide sleeve includes a substantially arc-shaped bent portion.

27. The implement of claim 26 wherein the arc-shaped bent portion covers an angular range of between 30 degrees and 150 degrees.

28. The implement of claim 26 wherein the arc-shaped bent portion covers an angular range of 90 degrees ±20 degrees.

29. The implement of claim 22 herein the elongate member together with the receiving sleeve are structured to be removably mounted to the handle member as a unit.

30. The implement of claim 17 further comprising a plurality of spherical enlargements located in spaced relationship on the intermediate portion of the shaft.

* * * * *